United States Patent [19]
Gadoua

[11] Patent Number: 4,744,514
[45] Date of Patent: May 17, 1988

[54] SCENTED LAPEL ORNAMENT

[76] Inventor: Susan M. Gadoua, 1911 Stellma La., Rochester, Mich. 48063

[21] Appl. No.: 903,601

[22] Filed: Sep. 5, 1986

[51] Int. Cl.[4] .............................................. A61L 9/04
[52] U.S. Cl. ...................................... 239/36; 239/56; 63/DIG. 2; 428/905
[58] Field of Search ............... 63/DIG. 1, DIG. 2, 2; 239/36, 55, 56, 53, 57, 60; 428/905, 79

[56] References Cited

U.S. PATENT DOCUMENTS

| | | | |
|---|---|---|---|
| 477,217 | 6/1892 | McCoy | 63/DIG. 2 |
| 2,141,402 | 12/1938 | Muller | 24/5 |
| 2,615,754 | 10/1952 | Lindenberg | 239/36 |
| 2,626,833 | 1/1953 | Valentine | 239/36 |
| 3,412,907 | 11/1968 | Faso | 428/905 |
| 3,441,353 | 4/1969 | Claff | 63/DIG. 2 |
| 3,509,003 | 4/1970 | Engle | 428/79 X |
| 3,896,995 | 7/1975 | Lelicoff | 239/36 |
| 4,228,954 | 10/1980 | Rosenzweig | 428/905 |
| 4,283,011 | 8/1981 | Spector | 239/36 |
| 4,356,969 | 11/1982 | Obermayer | 239/6 |

Primary Examiner—Richard J. Johnson
Attorney, Agent, or Firm—Krass & Young

[57] ABSTRACT

A laminated, flexible, lightweight scent-carrying ornament having an adhesive backing which permits the ornament to be applied to one's personal clothing. The laminated construction comprises an open weave top lamination, an absorbent center lamination, and an adhesive backed bottom lamination, all of the laminations being joined or fused together to form a single unit.

4 Claims, 1 Drawing Sheet

SCENTED LAPEL ORNAMENT

INTRODUCTION

This invention relates to scent-carrying clothing ornaments and particularly to a soft flexible scent-carrying clothing ornament having an adhesive backed lamination.

BACKGROUND OF THE INVENTION

The expected and usual application of scented fluids such as perfumes, colognes and toilet waters involves the direct application of such fluids to one's skin. It is known, however, that a stronger and/or longer lasting application of the scented fluid may be made by applying the fluid to an absorbent material such as a cotton-ball and placing the ball in one's clothing.

The prior art discloses more elaborate applications of scented fluids not only to provide a stronger and/or longer lasting scent but also to eliminate the necessity for direct contact between the scented fluid and one's skin; this may be especially advantageous in the case of persons with allergic reactions to scented fluids. By way of example U.S. Pat. No. 331,937 to W. H. Birge discloses a button, stud or charm defining a receptacle which may be charged by pouring the scented liquid or fluid into it and carried on the person. U.S. Pat. No. 2,109,092 to Roll discloses a rigid plastic trinket or ornament which is similarly capable of carrying a scent. Numerous patents including U.S. Pat. No. 3,270,525 to Sellers and U.S. Pat. No. 1,267,067 to Flagg discloses items of jewelry defining enclosures or receptacles which may be charged with the scented fluid and worn as trinkets, ornaments or, most commonly ear rings.

The articles of each of the above mentioned patents suffer the common disadvantage of rigid and relatively heavy, expensive construction and, except where a pin or clasp is provided, are not susceptible of direct and simple application to one's clothing.

SUMMARY OF THE INVENTION

The present invention comprises a scented ornament of flexible, lightweight and flexible laminated construction which may be easily applied to and worn on the lapel or other suitable location of one's personal clothing.

In general the invention comprises a soft flexible article of laminated construction comprising a permeable and decorative top lamination, an absorbent center lamination to receive and hold a scented fluid such as perfume, cologne or toilet water, and an adhesive backed impermeable cloth base lamination, all of said laminations being joined for form a single unit of decorative shape.

DETAILED DESCRIPTION OF THE PREFERRED EMBODIMENT

Figure 1:
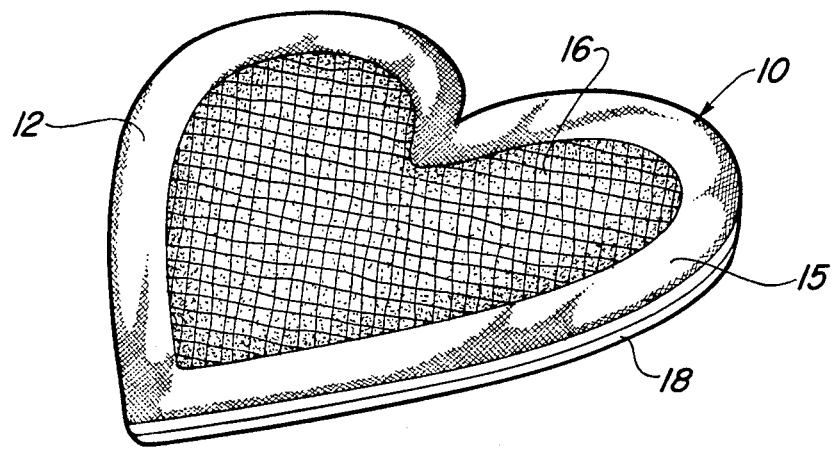
FIG. 1 is a perspective view of a decorative article constructed in accordance with the invention for direct adhesive application to one's clothing and capable of being charged with a selected scent.

Referring to the drawing there is shown an ornament 10 of flexible, laminated construction adapted to be worn on the lapel or other suitable location of one's personal clothing. In the illustrated embodiment the article 10 is formed in a decorative heart shape but it is to be understood that this shape is represented purely by way of example as an indefinite number of other desirable, appealing and attractive aesthetic shapes may also be employed.

Article 10 comprises a top lamination or layer 12, an absorbent center lamination 14 of cotton material or the like capable of being charged with and holding a scented fluid, and an impermeable base lamination 18 the exposed bottom surface of which is coated with an adhesive 20 of long lasting tacky material to allow the article 10 to be readily adhesively applied to one's personal clothing as well as to be removed easily from the clothing and transferred to another article of clothing.

All of the laminations 12, 14 and 18 are joined such as by pressure and heat welding to form a single integral unit of decorative shape, like weight and flexibility approaching if not equaling that of ordinary lightweight woven cloth.

The top lamination 12 is preferably formed of plastic mesh and comprises a border portion 15 which is tightly woven and a center portion of internal portion 16 which is very loosely woven to substantially increase permeability and to provide for the charging of the absorbent center lamination 14 with the preferred scent as well as to permit the scent to be released as the article is worn. A plastic material such as polyethylene is suitable.

The center lamination 14 as mentioned above is preferably formed of a soft, absorbent and flexible material such as cotton which is capable of receiving and absorbing an adequate quantity of scented fluid and to hold the fluid for gradual evaporation through the open weave portion 16 of the top lamination 12.

The bottom lamination 18 is preferably formed of non-permeable cloth such as a tightly woven Nylon or Rayon synthetic cloth or, alternatively, of a non-woven material of flexible synthetic fabrication.

Figure 2:
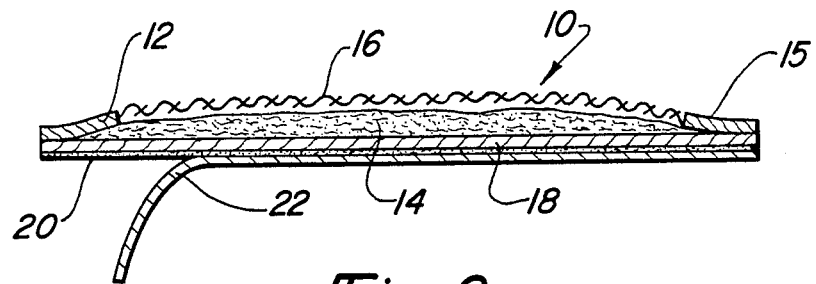
FIG. 2 is a sectional view of the article of FIG. 1.

As shown in the cross sectional view of FIG. 2 the laminations 12 and 18 are somewhat larger in dimension than the center lamination 14 so as to permit joining of the three laminations into a common unit at the peripheral edges such as by heat welding or adhesive bonding.

The adhesive layer 20 is applied to the exposed surface of the bottom lamination 18 and is of a tacky quality to permit the article 10 to be applied to one's clothing and to be removed and applied again.

The article 10 is preferably marketed with a protective plastic tape layer 22 over the adhesive layer 20.

In use, the user of the article 10 applies the desired scent through the open weave mesh center portion 16 of the top lamination 12 and thereafter removes the tape 22 which protects the adhesive layer 20. The article 10 may then be directly applied using light pressure to the lapel or other suitable location of one's clothing. The scent may be refreshing or recharged from time to time with the same or a different fluid. Alternatively, the article 10 may be sold with a scent already applied as a charge to the absorbent layer 14 in which case the article 10 is preferably sold in an air-tight plastic packet or envelope.

Again it is to be understood that the decorative heart shape of the article 10 is chosen purely by way of example and that an indefinite number of other decorative shapes, such as floral shapes, letters, numbers, and other symbols or insignias, may also be utilized.

I claim:

1. A rechargeable, scented ornament of essentially flat, flexible, laminated construction to be worn on a lapel or other location of person's clothing comprising:
    a permeable, decorative top lamination a first portion of which consists of loose, open net-like fabric and a second portion of which consists of tightly woven, substantially closed fabric;
    an absorbent center lamination, disposed immediately under, and held in place by, said top lamination, to receive and hold a charge of scented fluid; and
    an adhesive backed, impermeable cloth lamination disposed immediately under said center lamination and substantially coextensive with said top lamination;
    said laminations being joined to form a single essentially flat unit of decorative shape and cloth-like pliability.

2. The article of manufacture defined in claim 1 wherein the center lamination is cotton.

3. The article of manufacture defined in claim 1 wherein the top lamination is constructed at least partly at open-weave plastic mesh.

4. The article of manufacture defined in claim 1 further including a layer of protective tape over the adhesive portion of the adhesive backed impermeable cloth lamination to be removed prior to the application of said article to one's clothing.

* * * * *